United States Patent
Banner et al.

(10) Patent No.: US 6,796,305 B1
(45) Date of Patent: Sep. 28, 2004

(54) VENTILATOR MONITOR SYSTEM AND METHOD OF USING SAME

(75) Inventors: Michael J. Banner, Alachua, FL (US);
Paul B. Blanch, Alachua, FL (US);
Neil R. Euliano, Gainesville, FL (US);
Jose C. Principe, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 234 days.

(21) Appl. No.: 09/608,200

(22) Filed: Jun. 30, 2000

Related U.S. Application Data

(60) Provisional application No. 60/141,735, filed on Jun. 30, 1999.

(51) Int. Cl.$^7$ .............................................. A61M 16/00
(52) U.S. Cl. .......................... 128/204.21; 128/204.18; 128/204.23; 128/925
(58) Field of Search ....................... 128/204.18, 204.21, 128/204.23, 920, 924, 925, 915; 706/924

(56) References Cited

U.S. PATENT DOCUMENTS

| | | | |
|---|---|---|---|
| 3,595,226 A | 7/1971 | Newcombe | 128/142.2 |
| 4,537,190 A | 8/1985 | Caillot et al. | 128/204.22 |
| 4,565,194 A | 1/1986 | Weerda et al. | 128/204.23 |
| 4,813,431 A | 3/1989 | Brown | 128/748 |
| 4,986,268 A | 1/1991 | Tehrani | 128/204.22 |
| 4,990,894 A | 2/1991 | Loescher et al. | 340/573 |
| 5,107,831 A | 4/1992 | Halpern et al. | 128/204.26 |
| 5,161,525 A | 11/1992 | Kimm et al. | 128/204.26 |
| 5,307,795 A | 5/1994 | Whitwam et al. | 128/204.25 |
| 5,316,009 A | 5/1994 | Yamada | 128/716 |
| 5,320,093 A * | 6/1994 | Raemer | 128/203.12 |
| 5,331,995 A | 7/1994 | Westfall et al. | 137/8 |
| 5,335,650 A | 8/1994 | Shaffer et al. | 128/200.24 |
| 5,339,818 A | 8/1994 | Baker et al. | 128/677 |
| 5,365,922 A | 11/1994 | Raemer | 128/204.23 |
| 5,402,796 A | 4/1995 | Packer et al. | 128/719 |
| 5,429,123 A | 7/1995 | Shaffer et al. | 128/204.23 |
| 5,546,935 A | 8/1996 | Champeau | 128/205.23 |
| 5,549,106 A | 8/1996 | Gruenke et al. | 128/204.23 |

(List continued on next page.)

FOREIGN PATENT DOCUMENTS

| | | |
|---|---|---|
| DE | 44 10 508 A1 | 9/1994 |
| EP | 0 082 041 A1 | 6/1983 |
| EP | 0 504 725 A2 | 9/1992 |
| WO | WO 91/03979 | 4/1991 |
| WO | WO 95/164 B4 | 6/1995 |

*Primary Examiner*—Henry Bennett
*Assistant Examiner*—Mital Patel
(74) *Attorney, Agent, or Firm*—Saliwanchik, Lloyd & Saliwanchik

(57) ABSTRACT

The present invention provides a system and method for monitoring the ventilation support provided by a ventilator that is supplying a breathing gas to a patient via a breathing circuit that is in fluid communication with the lungs of the patient. The ventilator has a plurality of selectable ventilator setting controls governing the supply of ventilation support from the ventilator, each setting control selectable to a level setting. The ventilator support monitor system preferably receives at least one ventilator setting parameter signal, each ventilator setting parameter signal indicative of the level settings of one ventilator setting control, monitors a plurality of sensors, each sensor producing an output signal indicative of a measured ventilation support parameter, to determine the sufficiency of the ventilation support received by the patient, and determines the desired level settings of the ventilator setting controls in response to the received ventilator setting parameter signal and the output signals. The ventilator support monitor system preferably utilizes a trainable neural network to determine the desired level settings of the ventilator setting controls.

12 Claims, 9 Drawing Sheets

U.S. PATENT DOCUMENTS

| | | | | |
|---|---|---|---|---|
| 5,582,163 A | | 12/1996 | Bonassa | 128/204.26 |
| 5,584,291 A | | 12/1996 | Vapola et al. | 128/630 |
| 5,598,838 A | | 2/1997 | Servidio et al. | 128/204.23 |
| 5,678,539 A | * | 10/1997 | Schubert et al. | 128/204.21 |
| 5,692,497 A | | 12/1997 | Schnitzer et al. | 128/204.21 |
| 5,794,615 A | | 8/1998 | Estes | 128/204.23 |
| 5,884,622 A | | 3/1999 | Younes | 128/204.21 |
| 5,915,379 A | * | 6/1999 | Wallace et al. | 128/204.18 |
| 5,915,380 A | * | 6/1999 | Wallace et al. | 128/203.12 |
| 5,927,274 A | * | 7/1999 | Servidio et al. | 128/204.18 |
| 5,931,160 A | * | 8/1999 | Gilmore et al. | 128/204.18 |
| 6,158,430 A | * | 12/2000 | Pfeiffer et al. | 128/202.27 |
| 6,158,432 A | * | 12/2000 | Biondi et al. | 128/204.21 |
| 6,206,001 B1 | * | 3/2001 | Garber et al. | 128/201.22 |
| 6,305,372 B1 | * | 10/2001 | Servidio | 128/204.21 |
| 6,369,838 B1 | * | 4/2002 | Wallace et al. | 128/204.18 |

* cited by examiner

VENTILATOR MONITOR SYSTEM AND METHOD OF USING SAME

This application claims the benefit of provisional application No. 60/141,735 filed Jun. 30, 1999.

BACKGROUND OF THE INVENTION

1. Field of the Invention

The present invention relates to the respiratory care of a patient and, more particularly, to a ventilator monitor system that receives a plurality of ventilator support signals indicative of the sufficiency of ventilation support received by the patient, receives at least one ventilator signal indicative of the level settings of the ventilator setting controls of the ventilator, and determines the desired level settings of the ventilator setting controls of the ventilator to provide the appropriate quality and quantity of ventilation support to the patient.

2. Background

Mechanical ventilatory support is widely accepted as an effective form of therapy and means for treating patients with respiratory failure. Ventilation is the process of delivering oxygen to and washing carbon dioxide from the alveoli in the lungs. When receiving ventilatory support, the patient becomes part of a complex interactive system which is expected to provide adequate ventilation and promote gas exchange to aid in the stabilization and recovery of the patient. Clinical treatment of a ventilated patient often calls for monitoring a patient's breathing to detect an interruption or an irregularity in the breathing pattern, for triggering a ventilator to initiate assisted breathing, and for interrupting the assisted breathing periodically to wean the patient off of the assisted breathing regime, thereby restoring the patient's ability to breath independently.

In those instances in which a patient requires mechanical ventilation due to respiratory failure, a wide variety of mechanical ventilators are available. Most modern ventilators allow the clinician to select and use several modes of inhalation either individually or in combination via the ventilator setting controls that are common to the ventilators. These modes can be defined in three broad categories: spontaneous, assisted or controlled. During spontaneous ventilation without other modes of ventilation, the patient breathes at his own pace, but other interventions may affect other parameters of ventilation including the tidal volume and the baseline pressure, above ambient, within the system. In assisted ventilation, the patient initiates the inhalation by lowering the baseline pressure by varying degrees, and then the ventilator "assists" the patient by completing the breath by the application of positive pressure. During controlled ventilation, the patient is unable to breathe spontaneously or initiate a breath, and is therefore dependent on the ventilator for every breath. During spontaneous or assisted ventilation, the patient is required to "work" (to varying degrees) by using the respiratory muscles in order to breath.

The work of breathing (the work to initiate and sustain a breath) performed by a patient to inhale while intubated and attached to the ventilator may be divided into two major components: physiologic work of breathing (the work of breathing of the patient) and breathing apparatus imposed resistive work of breathing. The work of breathing can be measured and quantified in Joules/L of ventilation. In the past, techniques have been devised to supply ventilatory therapy to patients for the purpose of improving patient's efforts to breath by decreasing the work of breathing to sustain the breath. Still other techniques have been developed that aid in the reduction of the patient's inspiratory work required to trigger a ventilator system "ON" to assist the patient's breathing. It is desirable to reduce the effort expended by the patient in each of these phases, since a high work of breathing load can cause further damage to a weakened patient or be beyond the capacity or capability of small or disabled patients. It is further desirable to deliver the most appropriate mode, and, intra-mode, the most appropriate quality and quantity of ventilation support required the patient's current physiological needs.

The early generation of mechanical ventilators, prior to the mid-1960s, were designed to support alveolar ventilation and to provide supplemental oxygen for those patients who were unable to breathe due to neuromuscular impairment. Since that time, mechanical ventilators have become more sophisticated and complicated in response to increasing understanding of lung pathophysiology. Larger tidal volumes, an occasional "sigh breath," and a low level of positive end-expiratory pressure (PEEP) were introduced to overcome the gradual decrease in functional residual capacity (FRC) that occurs during positive-pressure ventilation (PPV) with lower tidal volumes and no PEEP. Because a decreased functional residual capacity is the primary pulmonary defect during acute lung injury, continuous positive pressure (CPAP) and PEEP became the primary modes of ventilatory support during acute lung injury.

In an effort to improve a patient's tolerance of mechanical ventilation, assisted or patient-triggered ventilation modes were developed. Partial PPV support, in which mechanical support supplements spontaneous ventilation, became possible for adults outside the operating room when intermittent mandatory ventilation (IMV) became available in the 1970s. Varieties of "alternative" ventilation modes addressing the needs of severely impaired patients continue to be developed.

The second generation of ventilators was characterized by better electronics but, unfortunately, due to attempts to replace the continuous high gas flow IMV system with imperfect demand flow valves, failed to deliver high flow rates of gas in response to the patient's inspiratory effort. This apparent advance forced patient to perform excessive imposed work and thus, total work in order to overcome ventilator, circuit, and demand flow valve resistance and inertia. In recent years, microprocessors have been introduced into modern ventilators. Microprocessor ventilators are typically equipped with sensors that monitor breath-by-breath flow, pressure, volume, and derive mechanical respiratory parameters. Their ability to sense and transduce "accurately," combined with computer technology, makes the interaction between clinician, patient, and ventilator more sophisticated than ever. The prior art microprocessor controlled ventilators suffered from compromised accuracy due to the placement of the sensors required to transduce the data signals. Consequently, complicated algorithms were developed so that the ventilators could "approximate" what was actually occurring within the patient's lungs on a breath by breath basis. In effect, the computer controlled prior art ventilators were limited to the precise, and unyielding, nature of the mathematical algorithms which attempted to mimic cause and effect in the ventilator support provided to the patient.

Unfortunately, as ventilators become more complicated and offer more options, the number of potentially dangerous clinical decisions increases. The physicians, nurses, and respiratory therapists that care for the critically ill are faced with expensive, complicated machines with few clear guidelines for their effective use. The setting, monitoring, and interpretation of some ventilatory parameters have become more speculative and empirical, leading to potentially hazardous misuse of these new ventilator modalities. For example, the physician taking care of the patient may decide to increase the pressure support ventilation (PSV) level based on the displayed spontaneous breathing frequency. This may result in an increase in the work of breathing of the patient which may not be appropriate. This "parameter-monitor" approach, unfortunately, threatens the patient with the provision of inappropriate levels of pressure support.

Ideally, ventilatory support should be tailored to each patient's existing pathophysiology, rather than employing a single technique for all patients with ventilatory failure (i.e., in the example above, of the fallacy of using spontaneous breathing frequency to accurately infer a patient's work of breathing). Thus, current ventilatory support ranges from controlled mechanical ventilation to total spontaneous ventilation with CPAP for support of oxygenation and the elastic work of breathing and restoration of lung volume. Partial ventilation support bridges the gap for patients who are able to provide some ventilation effort but who cannot entirely support their own alveolar ventilation. The decision-making process regarding the quality and quantity of ventilatory support is further complicated by the increasing knowledge of the effect of mechanical ventilation on other organ systems.

The overall performance of the assisted ventilatory system is determined by both physiological and mechanical factors. The physiological determinants, which include the nature of the pulmonary disease, the ventilatory efforts of the patient, and many other physiological variables, changes with time and are difficult to diagnosis. Moreover, the physician historically had relatively little control over these determinants. Mechanical input to the system, on the other hand, is to a large extent controlled and can be reasonably well characterized by examining the parameters of ventilator flow, volume, and/or pressure. Optimal ventilatory assistance requires both appropriately minimizing physiologic workloads to a tolerable level and decreasing imposed resistive workloads to zero. Doing both should insure that the patient is neither overstressed nor oversupported. Insufficient ventilatory support places unnecessary demands upon the patient's already compromised respiratory system, thereby inducing or increasing respiratory muscle fatigue. Excessive ventilatory support places the patient at risk for pulmonary-barotrauma, respiratory muscle deconditioning, and other complications of mechanical ventilation.

Unfortunately, none of the techniques devised to supply ventilatory support for the purpose of improving patient efforts to breath, by automatically decreasing imposed work of breathing to zero and appropriately decreasing physiologic work once a ventilator system has been triggered by a patient's inspiratory effort, provides the clinician with advice in the increasingly complicated decision-making process regarding the quality and quantity of ventilatory support. As noted above, it is desirable to reduce the effort expended by the patient to avoid unnecessary medical complications of the required respiratory support and to deliver the most appropriate mode, and, intra-mode, the most appropriate quality and quantity of ventilation support required the patient's current physiological needs. Even using the advanced microprocessor controlled modem ventilators, the prior art apparatus and methods tend to depend upon mathematical models for determination of necessary actions. For example, a ventilator may sense that the hemoglobin oxygen saturation level of the patient is inappropriately low and, from the sensed data and based upon a determined mathematical relationship, the ventilator may determine that the oxygen content of the breathing gas supplied to the patient should be increased. This is similar to, and unfortunately as inaccurate as, a physician simply looking at a patient turning "blue" and determining more oxygen is needed.

From the above, in the complicated decision-making environment engendered by the modem venilator, it is clear that it would be desirable to have a medical ventilator monitor system that alerts the clinician of the ventilator's failure to supply the appropriate quality and quantity of ventilatory support and provides advice to the clinician regarding the appropriate quality and quantity of ventilatory support that is tailored to the patient's pathophysiology. Such a ventilatory monitor system is unavailable in current systems.

SUMMARY

In accordance with the purposes of this invention, as embodied and broadly described herein, this invention, in one aspect, relates to a method of monitoring the ventilation support provided by a ventilator that is supplying a breathing gas to a patient via a breathing circuit that is in fluid communication with the lungs of the patient. The ventilator has a plurality of selectable ventilator setting controls governing the supply of ventilation support from the ventilator, each setting control selectable to a level setting. The ventilator support monitor system preferably receives at least one ventilator setting parameter signal, each ventilator setting parameter signal indicative of the level settings of one ventilator setting control, monitors a plurality of sensors, each sensor producing an output signal indicative of a measured ventilation support parameter, to determine the sufficiency of the ventilation support received by the patient, and determines the desired level settings of the ventilator setting controls in response to the received ventilator setting parameter signal and the output signals. The ventilator support monitor system preferably utilizes a trainable neural network to determine the desired level settings of the ventilator setting controls.

In another aspect, the invention relates to a ventilator support monitor system that supplies a breathing gas to a patient via a breathing circuit in fluid communication with the ventilator and the lungs of a patient. The ventilator preferably has at least one selectable ventilator setting control. The selectable ventilator setting control governs the supply of ventilation support from the ventilator to the patient via the breathing circuit. Each ventilator setting control generates a ventilator setting parameter signal indicative of the current level setting of the ventilator setting.

The ventilator support monitor system has a plurality of sensors and a processing subsystem. The sensors measure a plurality of ventilation support parameters and each sensor generates an output signal based on the measured ventilation support parameter. The processing subsystem is connected to receive the output signal from the sensor and the ventilator setting signal(s) from the ventilator setting control(s). The processor of the processing subsystem runs under control of a program stored in the memory of the processing subsystem and determines a desired level setting of at least one ventilator setting control in response to the ventilator setting parameter signal and the output signal. The processing subsystem of the ventilator preferably utilizes a trainable neural network to determine the desired level settings of the ventilator setting controls.

DETAILED DESCRIPTION OF THE FIGURES

The accompanying drawings, which are incorporated in and constitute a part of this specification, illustrate several embodiments of the invention and together with the description, serve to explain the principals of the invention.

DETAILED DESCRIPTION OF THE INVENTION

The present invention is more particularly described in the following examples that are intended to be illustrative only since numerous modifications and variations therein will be apparent to those skilled in the art. As used in the specification and in the claims, the singular form "a," "an" and "the" include plural referents unless the context clearly dictates otherwise.

Figure 1:
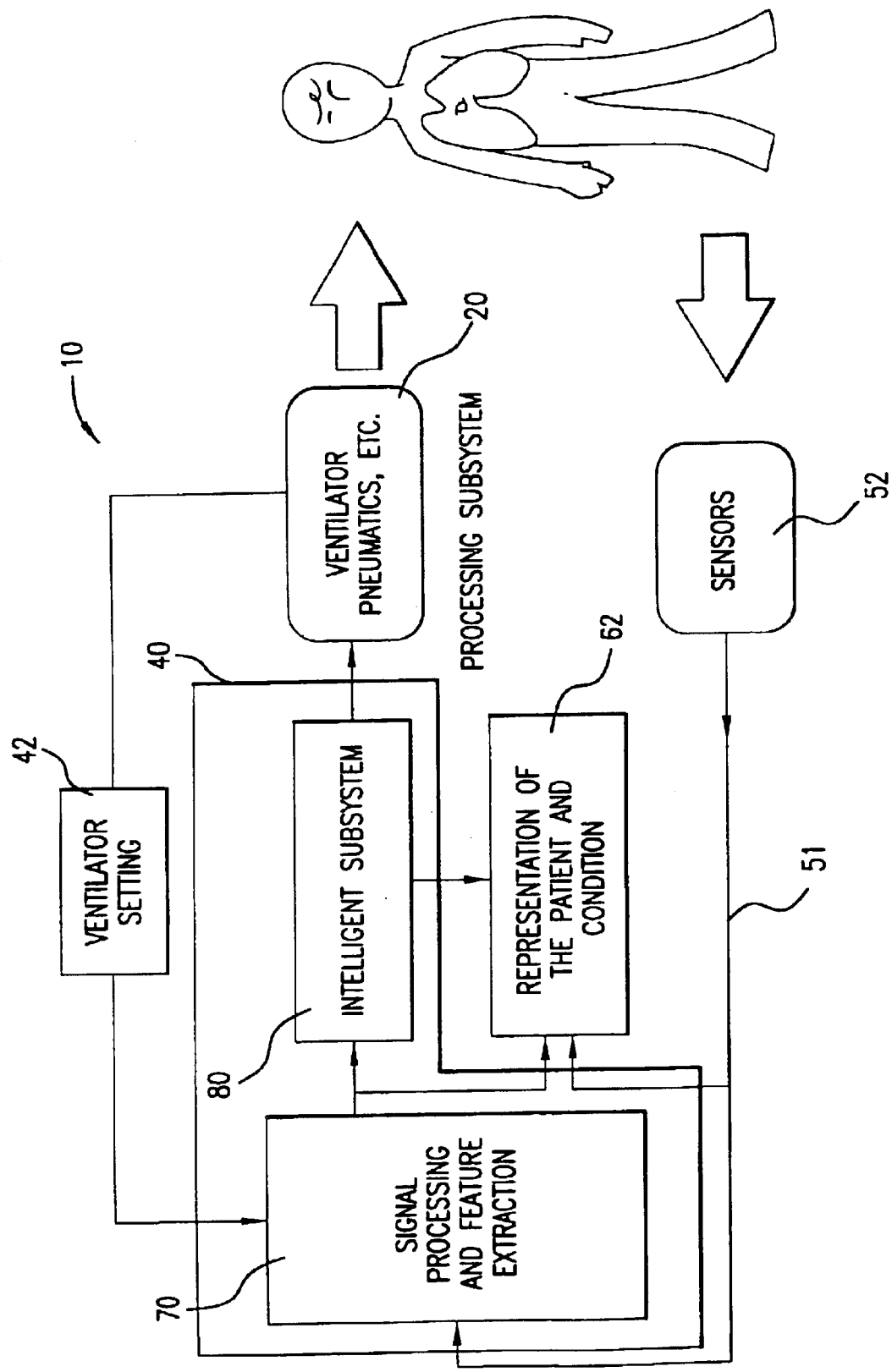
FIG. 1 is a block diagram of one configuration a ventilator monitor system for determining the desired ventilator control settings of a ventilator.
Figure 2A:
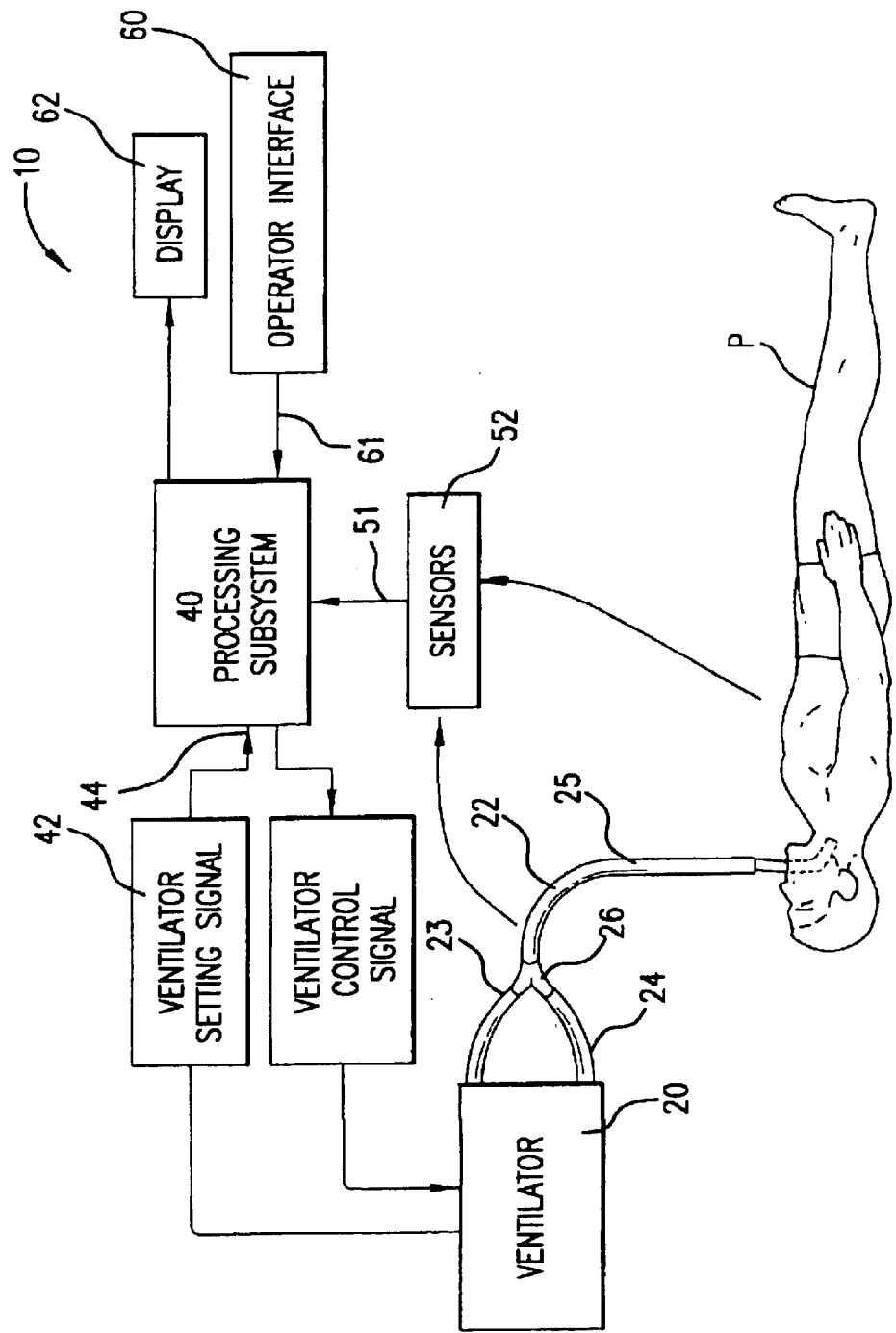
FIG. 2A is a block diagram of one configuration of the ventilator monitor system showing the ventilator providing ventilation support to a patient connected to the ventilator via a breathing circuit.
Figure 2B:
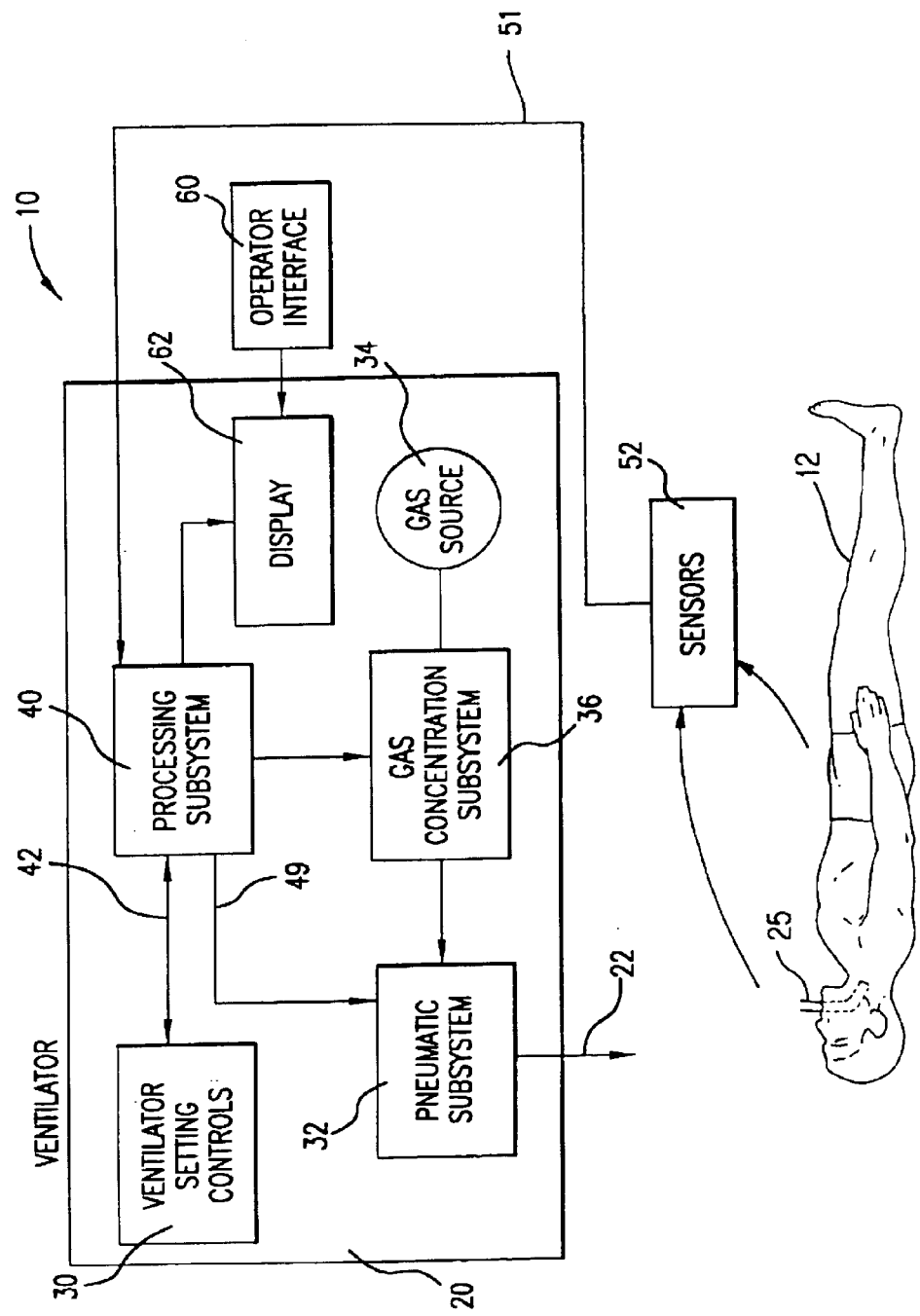
FIG. 2B is a block diagram of an embodiment of a ventilator monitor system showing the monitor system incorporated into the ventilator.
Figure 3:
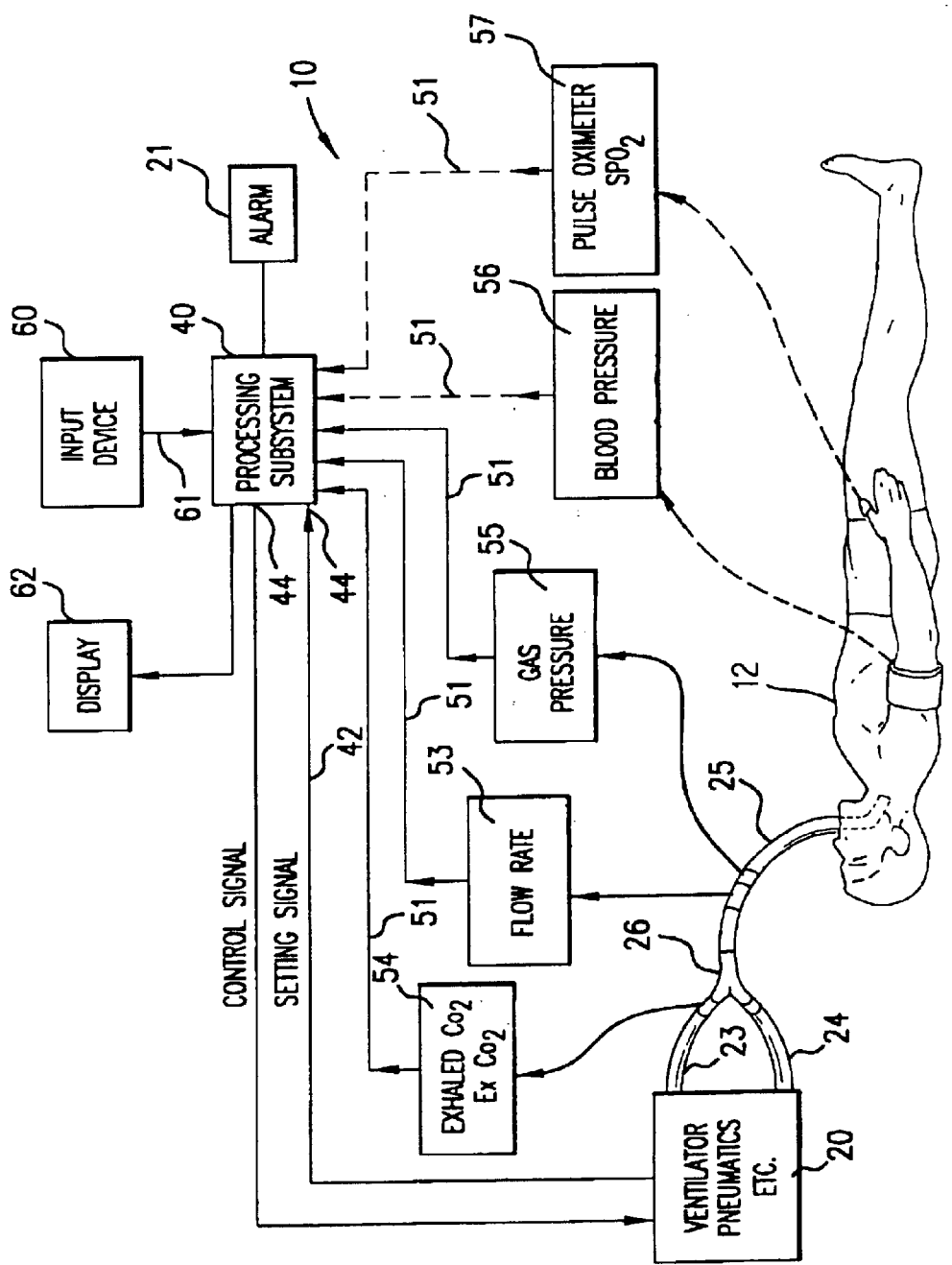
FIG. 3 is a block diagram of the ventilator monitor system showing a plurality of sensors connected to the processing subsystem.

As depicted in FIGS. 1–3, the ventilator monitor system 10 of the present invention preferably comprises a conventional ventilator 20, a processing subsystem 40, a measuring system, and a display 62. The ventilator 20 supplies a breathing gas to the lungs of the patient P via a breathing circuit 22 that typically comprises an inspiratory line 23, an expiratory line 24, and a patient connection tube 25, all connected by a patient connector 26. The preferred ventilator 20 is a microprocessor-controlled ventilator of a type that is exemplified by a Mallinckrodt, Nelcor, Puritan-Bennet, 7200ae, or a Bird 6400 Ventilator.

To control the delivery of the breathing gas, the preferred ventilator 20 typically has at least one selectable ventilator setting control 30 operatively connected to the processing system 40 for governing the supply of ventilation support provided to the patient P. As one skilled in the art will appreciate, each ventilator setting control 30 is selectable to a desired level setting. Such a ventilator 20 is particularly useful in controlling the delivery of breathing support so that the quantity and quality of ventilation support coincides with the physiological support needs of the patient P.

In the preferred embodiment, the preferred ventilator 20 can operate selectively in one or more conventional modes, as needed and selected by the operator and/or the processing subsystem 40, including but not limited to: (i) assist control ventilation (ACMV); (ii) sychronized intermittent mandatory ventilation (SIMY); (iii) continuous positive airway pressure (CPAP); (iv) pressure-control ventilation (PCV); (v) pressure support ventilation (PSV); (vi) proportional assist ventilation (PAV); and (vii) volume assured pressure support (VAPS). Further, the level setting of one or more conventional ventilator setting controls 30 of the ventilator 20 (i.e., the intra-mode setting controls of the ventilator 20) may be adjusted, as needed and selected by the operator and/or the processing system 40 in order to maintain the sufficiency of ventilation support delivered to the patient P. The ventilator setting controls 30 of the ventilator 20 include but are not limited to controls for setting: (i) a minute ventilation (Ve) level; (ii) a ventilator breathing frequency (f) level; (iii) a tidal volume ($V_T$) level; (iv) a breathing gas flow rate (V) level; (v) a pressure limit level; (vi) a work of breathing (WOB) level; (vii) a pressure support ventilation (PSV)level; (viii) a positive end expiratory pressure (PEEP) level; (ix) a continuous positive airway pressure (CPAP) level; and (x) a fractional inhaled oxygen concentration (FIO2) level.

The conventional ventilator 20 contemplated typically has a gas delivery system and may also have a gas composition control system. The gas delivery system may, for example, be a pneumatic subsystem 32 in fluid/flow communication with a gas source 34 of one or more breathing gases and the breathing circuit 22 and in operative connection with the ventilator control settings 30 of the ventilator 20 and the processing subsystem 40. The breathing circuit 22 is in fluid communication with the lungs of the patient P. As one skilled in the art will appreciate, the pneumatic subsystem 40 of the ventilator 20 and the operative connection of that pneumatic subsystem 40 to the source of breathing gas 34 of the ventilator 20 may be any design known in the art that has at least one actuator (not shown) that is capable of being operatively coupled, preferably electrically coupled, to the ventilator setting controls 30 for control of, for example, the flow rate, frequency, and/or pressure of the breathing gas delivered by the ventilator 20 to the patient P from the gas source 34. Such a pneumatic system 32 is disclosed in U.S. Pat. No. 4,838,259 to Gluck et al., U.S. Pat. No. 5,303,698 to Tobia et al., U.S. Pat. No. 5,400,777 to Olsson et al., U.S. Pat. No. 5,429,123 to Shaffer et al., and U.S. Pat. No. 5,692,497 to Schnitzer et al., all of which are incorporated in their entirety by reference herein and is exemplified by the Mallinckrodt, Nelcor, Puritan-Bennet, 7200ae, and the Bird 6400 Ventilator.

The gas composition control system may, for example, be an oxygen control subsystem 36 coupled to the source of breathing gas 34 and in operative connection to the ventilator setting controls 30 of the ventilator 20 and the processing subsystem 40. The oxygen control subsystem 36 allows for the preferred control of the percentage composition of the gases supplied to the patient P. As one skilled in the art will appreciate, the oxygen control subsystem 36 of the ventilator 20 and the operative connection of that oxygen control subsystem 36 to the pneumatic subsystem 32 and to the source of breathing gas 34 of the ventilator 20 may be any design known in the art that has at least. one actuator (not shown) that is capable of being operatively coupled, preferably electrically coupled, to the ventilator setting controls 30 for control of, for example, the percentage composition of the oxygen supplied to the patient P.

The processing subsystem 40 of the ventilator monitor system 10 preferably has an input 44 that is operatively coupled to the ventilator setting controls 30 of the ventilator 20 so that at least one ventilator setting parameter signal 42 may be received by the processing subsystem 40. Each ventilator setting parameter signal 42 is preferably indicative of a setting of a ventilator setting control 30. Thus, the processing system 40 is in receipt of signals 42, preferably continuously, indicative of the current level settings of the ventilator setting controls 30. As one skilled in the art will appreciate, the current level settings of the ventilator setting controls 30 may be stored in the memory of the processing subsystem 40. In this example, the ventilator setting parameter signals 42 would be input from the memory of the processing subsystem 40 to the processor for continued processing and assessment.

For example, the input of the processing system 40 may receive one or more of the following ventilator setting parameter signals 42: a minute ventilation ($V_E$) signal indicative of the $V_E$ level set on the ventilator 20; a ventilator breathing frequency (f) signal indicative of the f level set on the ventilator 20; a tidal volume ($V_T$) signal indicative of the $V_T$ level set on the ventilator 20; a breathing gas flow rate (V) signal indicative of the V level set on the ventilator 20; a pressure limit signal indicative of the pressure limit set on the ventilator 20; a work of breathing (WOB) signal indicative of the WOB level set on the ventilator 20; a pressure support ventilation (PSV) signal indicative of the PSV level set on the ventilator 20; a positive end expiratory pressure (PEEP) signal indicative of the PEEP level set on the ventilator 20; a continuous positive airway pressure (CPAP) signal indicative of the CPAP level set on the ventilator 20; and a fractional inhaled oxygen concentration (FIO2) signal indicative of the FIO2 level set on the ventilator 20.

The measuring system of the monitor system 10 is also operatively connected to the processing subsystem 40. The measuring system senses and measures a plurality of ventilation support parameters which are indicative of the ventilation support provided to the patient P and the physiological condition of the patient P. It is contemplated that the measuring system may comprise at least one sensor 52, and preferably comprises a-plurality of sensors 52, for capturing the desired ventilation support data. Each sensor 52 generates an output signal 51 based on the particular measured ventilation support parameter.

In one preferred embodiment shown in FIG. 3, the processing subsystem 30 is shown operatively connected to a plurality of sensors such as a flow rate sensor 53, an exhaled CO2 (ex CO2) sensor 54, a pressure sensor 55, a blood pressure sensor 56, and a SPO2 sensor 57. In this embodiment, it is preferred that the monitor system 10 be responsive to the output signals 51 input into the processing subsystem 40 from, for example: i) the flow rate sensor 53 which is indicative of the flow rate ventilation support parameter of the gas expired/inspired by the patient P within the breathing circuit 22, ii) the gas pressure sensor 55 which is indicative of the pressure ventilation support parameter of the breathing gas within the breathing circuit 22, and iii) the Ex CO2 sensor 54 which is indicative of the exhaled carbon dioxide ventilation support parameter present in the exhaled gas expired by the patient P within the breathing circuit 22 (i.e., the flow rate output signal 51 generated by the flow rate sensor 53, the gas pressure output signal 51 generated by the gas pressure sensor 55, and the Ex CO2 output signal 51 generated by the Ex CO2 sensor 54). Optionally, the monitor system 10 may be responsive to output signals 51 input into the processing subsystem 40 from the output of the blood pressure sensor 56, which is indicative of the blood pressure ventilation support parameter of the patient P, for example the arterial systolic, diastolic, and mean blood pressure of the patient P, and the SPO2 sensor 57 which is indicative of the hemoglobin oxygen saturation level ventilation support parameter of the patient P (ie., the blood pressure output signal 51 generated by the blood pressure sensor 56 and the SPO2 output signal 51 generated by the SPO2 sensor 57).

The flow rate sensor 53, the pressure sensor 55, and the Ex CO2 sensor 54 are preferably positioned between the patient connector 26 and the patient connection tube 25. Alternatively, it is preferred that the pressure sensor 55 be located at the tracheal end of the patient connection tube 25. The flow rate, pressure, and Ex CO2 sensors 53, 55, 54 are exemplified by Novametrics, $CO_2$SMO+monitor (which has flow rate, pressure, and ExCO2 sensors). The blood pressure sensor 56 and the SPO2 sensor 57 are exemplified by Dynamap, Inc.'s blood pressure sensor and Novametrics, $CO_2$SMO+monitor's SPO2 sensor. The blood pressure sensor 56 and the SPO2 sensor 57 may be attache dot a portion of the patient's body to render the requisite measurements. For example, the blood pressure sensor 56, here for example shown as a blood pressure cuff, is shown attached to, the arm of the patient P and the SPO2 sensor 57, which may, for example, be a pulse oximeter, is shown attached to a finger of the patient 12. One skilled in the art will appreciate the blood pressure data maybe derived form the SPO2 sensor 57 which eliminates the need for the blood pressure sensor 56.

Additional standard equipment can include an operator interface 60, which in the preferred embodiment is a membrane keypad, a keyboard, a mouse, or other suitable input device, for providing user inputs of both data and control commands needed to execute the software which implements the various functions of the invention. The operator of the ventilator monitor system 10 of the present invention may provide the processing subsystem 40, via an operator input signal generated by the operator interface 60, with any number of applicable input parameters, such as patient identification information, patient age, patient weight, or other desired patient statistics. It is preferred that the operator input predetermined patient reference data, such as the arterial blood gas ph, the arterial blood gas PaO2, and/or the arterial blood gas PaCO2 of the patient's blood, and/or patient's temperature into the processing subsystem 40 as operator input signals 61 via the operator interface 60. The monitor system 10 may also be responsive to the core body temperature of the patient P which may be input into the processing subsystem 40 as an output signal 51 from a temperature sensor 58 attached to the patient P or as an operator input signal 61 via the operator interface 60.

The processing subsystem 40 preferably comprises a processor 46, for example a microprocessor, a hybrid hardware/software system, controller, or computer, and a memory. The output signals 51 and the ventilation data 72 derived from the output signals 51 are stored in the memory of the processing subsystem 40 at user-defined rates, which may be continuous, for as-needed retrieval and analysis. The ventilator setting signal 42 may also be stored in the memory at a user-defined rate. As one skilled with the art will appreciate, any generated signal may be stored in the memory at user-defined rates. The memory may be, for example, a floppy disk drive, a CD drive, internal RAM or hard drive of the associated processor 12.

The processing subsystem 40 is responsive to the output signals 51 of the measuring means, the ventilator setting parameter signal(s) 42, and, if provided, the operator input signals 61. The processor 46 runs under the control of a program stored in the memory and has intelligent programming for the determination of at least one desired level setting of the ventilator setting controls 30 based on at least a portion of the output signal 51 from the measuring means, at least a portion of the ventilator setting parameter signal(s) 42 received at the input 44 of the processing subsystem 40, and, if provided, at least a portion of the operator input signals 61.

The desired level settings for the ventilator setting controls 30 of the ventilator 20 may include at least one of the group of: i) a minute ventilation ($V_E$) level indicative of the desired $V_E$ level to set on the ventilator 20; ii) a ventilator breathing frequency (f) level indicative of the desired f level to set on the ventilator 20; iii) a tidal volume ($V_T$) level indicative of the $V_T$ level to set on the ventilator 20; iv) a breathing gas flow rate (V) level indicative of the V level to set on the ventilator 20; v) a pressure limit level indicative of the pressure limit level to set on the ventilator 20; vi) a work of breathing (WOB) level indicative of the WOB level to set on the ventilator 20; vii) a pressure support ventilation (PSV) level indicative of the PSV level to set on the ventilator 20; viii) a positive end expiratory pressure (PEEP) level indicative of the PEEP level to set on the ventilator 20; ix) a continuous positive airway pressure (CPAP) level indicative of the CPAP level to set on the ventilator 20; and x) a fractional inhaled oxygen concentration (FIO2) level indicative of the FIO2 level to set on the ventilator 20.

The desired level setting of the ventilator setting controls 30 determined by the processing system 40 of the monitor system 10 may be displayed to the operator via the display. The display of the monitor system 10 preferably comprises a visual display 62 or CRT, electronically coupled to the processing subsystem 40 for outputting and displaying output display signals generated from the processing subsystem 40.

Still further, the monitor system 10 may have an alarm 21 for alerting the operator of either a failure of the monitor system 10, such as a power failure of loss of signal data input, or an inappropriate setting of a ventilator control 30, such as a level setting of a ventilator setting control 30 currently controlling the delivery of ventilator support to the patient P differing from a recommended desired level setting of the ventilator setting control 30. Preferably, the alarm 21 comprises a visual and/or audio alarm, but any means for alerting the operating clinician know to one skilled in the art may be used. Of course, it is desired to use a backup power supply, such as a battery.

Figure 4:
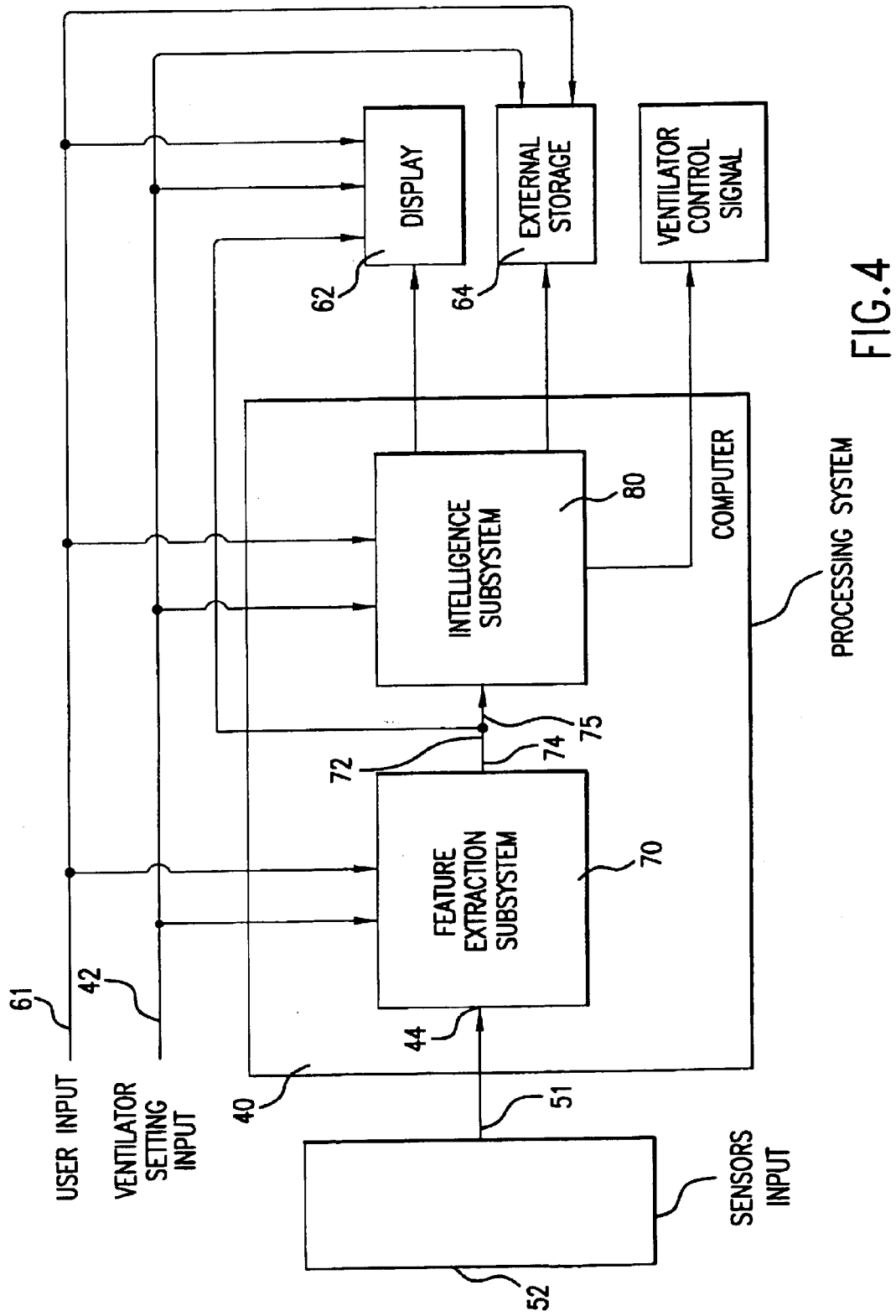
FIG. 4 is a block diagram of a processing subsystem of the present invention.
Figure 5:
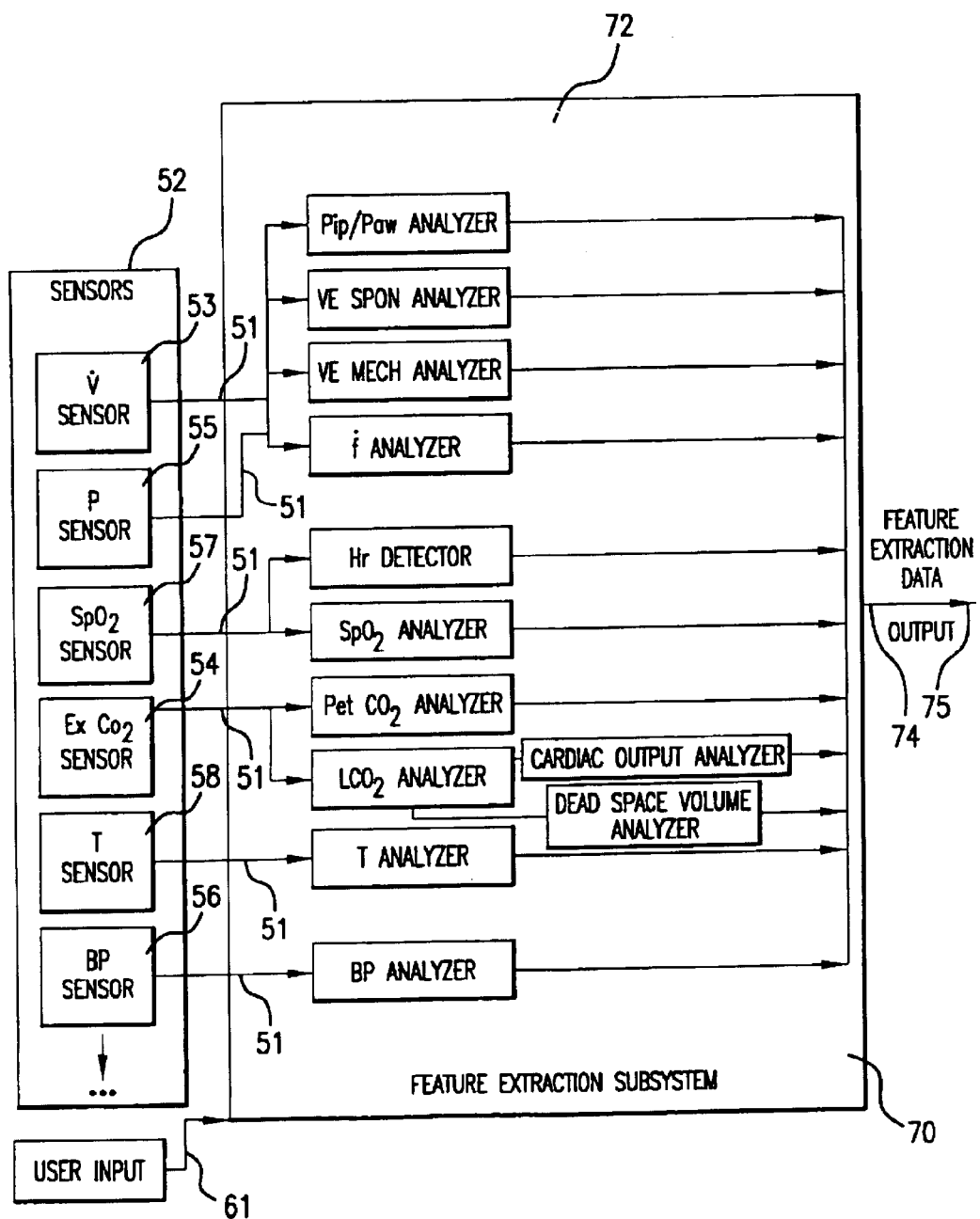
FIG. 5 is a block diagram of a feature extraction subsystem of the present invention.

Referring to FIGS. 4 and 5, the processing subsystem of the preferred embodiment of the present invention has a means for determining the desired ventilation control settings 30 of the ventilator 20. The determining means preferably comprises a feature extraction subsystem 70 and an intelligence subsystem 80. The feature extraction subsystem 70 has a means for extracting and compiling pertinent ventilation data features from the input of the measuring means (i.e., the output signals 51). In effect, the feature extraction subsystem 70 acts as a preprocessor for the intelligence subsystem 80. An example of the feature extraction subsystem 70 is shown in FIG. 5. Here, a flow rate sensor 53, a gas pressure sensor 55, a SPO2 sensor 57, an Ex CO2 sensor 54, a temperature (T) sensor 58, a blood pressure (BP) sensor 56, of a type described above, and any other desired sensor are operatively connected to the feature extraction subsystem 70 of the processing subsystem 40. Preferably, the flow rate sensor 53, the gas pressure sensor 55, and the Ex CO2 sensor 54 provide the only inputs to the monitor system. The other sensor inputs, and the user input, may be included to increase the reliability and confidence of the determined desired level settings of the controls 30. The monitor system 10 preferably adjusts the extraction of ventilator data 72 as a function of the presence or absence of these optional inputs. By making the number of inputs optional, which also makes the required number of sensors 52 comprising the measuring system optional, the number of environments in which the ventilator monitor system 10 can be used is increased.

The purpose of the feature extraction subsystem 70 is to calculate and/or identify and extract important variables or features from the output signals 51 produced by the measuring means. For example, from the exemplified required inputs to the feature extraction subsystem 70, i.e., the gas pressure output signal 51, the flow rate output signal 51, and the Ex CO2 output signal 51, a plurality of ventilation data 72 may be derived. The derived ventilation data 72 may comprise: the values of any output signals 51 used, such as, for example, the gas pressure output signal 51, the flow rate output signal 51, and the Ex CO2 output signal 51 output signals 51; the peak inflation pressure (PIP), which is the maximal pressure generated during mechanical ventilation of the lungs; the mean airway pressure (PAW), which is the average positive pressure measured at the airway opening in the patient connection tube 25 or in the breathing circuit 22 over one minute; the positive end expiratory pressure (PEEP), which is the baseline or starting positive pressure prior to mechanical inflation or the positive pressure applied continuously during inhalation and exhalation during spontaneous ventilation; breathing frequency (f), which is the frequency or rate or breathing per minute (the total breathing frequency $f_{TOT}$ is the sun of the mechanical $f_{MECH}$ ventilator preselected frequency and the spontaneous $f_{SPON}$ patient breathing frequency);, the tidal volume ($V_T$), which is the volume of the breathing gas moving in and out of the lungs per breath ($V_{T\ MECH}$ is the ventilator preselected $V_T$ per breath and $V_{T\ SPON}$ is the inhaled and exhaled volume per breath of the patient); the minute exhaled ventilation ($V_E$), which is the volume of breathing gas moving in and out of the lungs of the patient per minute ($V_E$ is the product of the breathing frequency f and the tidal volume ($V_E = f \times V_T$), and the $V_{E\ TOT}$ is the sum of the ventilator preselected $V_E$ ($V_{E\ MEC}$) and the spontaneous patient $V_E$ inhaled and exhaled per minute ($V_{E\ SPON}$)); the inhalation-to-exhalation time ratio (I:E ratio), which is the ratio of inhalation time to exhalation tiem during mechanical ventilation; the physiologic dead space volume ($V_{Dphys}$), which is the volume of gas in the anatomic airway and in ventilated, unperfused alveoli that does not participate in blood gas exchange; the lung carbon dioxide elimination rate (LCO2), which is the volume of CO2 exhaled per breath or per minute (LCO2 is the area under the Ex CO2 and volume curve); the partial pressure end-tidal carbon dioxide level (PetCO2), which is the partial pressure of the exhaled CO2 measured at the end of the exhalation; the cardiac output (CO) of the patient, which is the amount of blood ejected from the heart per minute and which may, for example be derived from the determined LCO2 rate; the respiratory system compliance and resistance; the respiratory muscle pressure, the work of breathing of the patient which may be derived from the determined respiratory muscle pressure; and pressure-volume loops.

Ventilation data 72 may also be derived from the exemplified optional inputs to the feature extraction subsystem 70. From the SPO2 output signal 51, the arterial blood hemoglobin oxygen saturation level and the heart rate may be determined, and the pulsatile blood pressure waveform of the SPO2 output signal 51 may be used to determine arterial blood pressure. Additionally, from the blood pressure output signal 51, the arterial systolic, diastolic and mean blood pressure of the patient P may be determined. Further, from the temperature output signal 51, the core body temperature of the patient may 12 be derived. Still further, from the arterial blood hemoglobin oxygen saturation level and the determined LCO2, the dead space volume may be determined.

The feature extraction subsystem 70 may also receive user input via the operator interface 60 and may receive the ventilator setting parameter signal 42. The ventilation data 72 is preferably compiled in the feature extraction subsystem 70 and a feature vector 74 or matrix is preferably generated which contains all of the ventilation data items used by the monitor subsystem 10 to perform the ventilation support assessment process. The feature vector 74 may be updated at user-defined intervals such as, for example, after each breath or each minute and is output from the feature extraction subsystem 70 to the intelligence subsystem 80 as a ventilation data output signal 75. Alternatively, as one skilled in the art will appreciate, the ventilation data 72 may be directly outputted to the intelligence subsystem 80 as the ventilation data output signal 75 without the intervening step of generating the feature vector 74 or matrix. The ventilation data 72 may also be outputted to the display 62.

Figure 6:
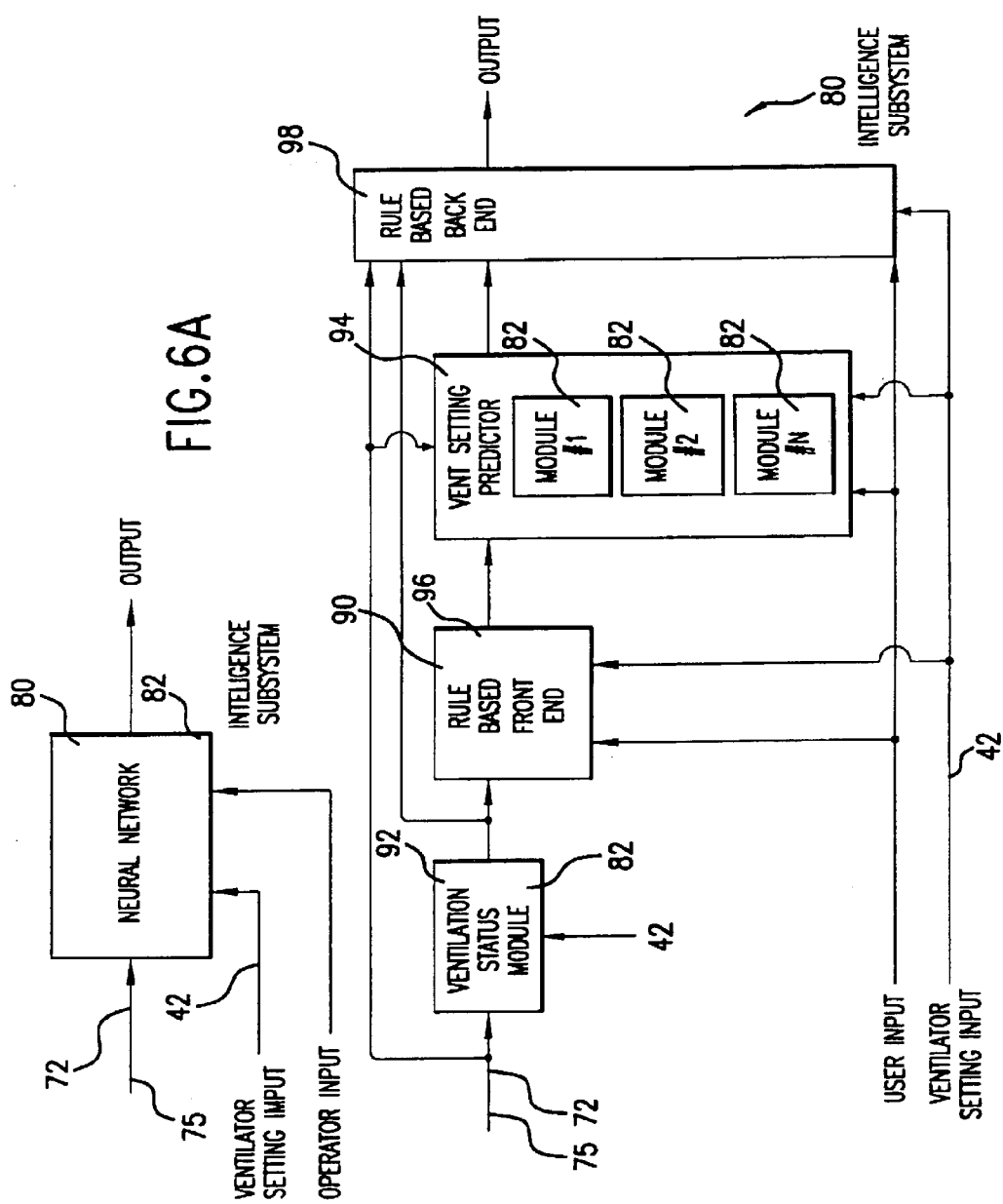
FIG. 6A is a block diagram of one embodiment of the intelligence subsystem of the processing subsystem.
FIG. 6B is a block diagram of a second embodiment of the intelligence subsystem of the processing subsystem.

Referring to FIGS. 4, 6A and 6B, the intelligence subsystem 80 of the processing subsystem 40 preferably has a neural network 82. The primary function of the intelligence subsystem 80 is to make an assessment of the ventilator support provided to the patient and, based upon the assessment, recommend the desired level settings of the ventilator setting controls 30 which will adequately, and preferably optimally, support the physiological ventilation support needs of the patient P. For example, as shown in FIG. 6A, the intelligence subsystem 80 of the processing subsystem 40 may have a neural network 82 that recieves the ventilation data output signal 75 containing the compiled ventilation data 72. The neural network 82 also receives the ventilator setting parameter signal 42 and may receive user input from the operator interface 60.

To fully appreciate the various aspects and benefits produced by the present invention, a basic understanding of neural network technology is required. Following is a brief discussion of this technology, as applicable to the ventilator monitor system 10 and method of the present invention.

Figure 8:
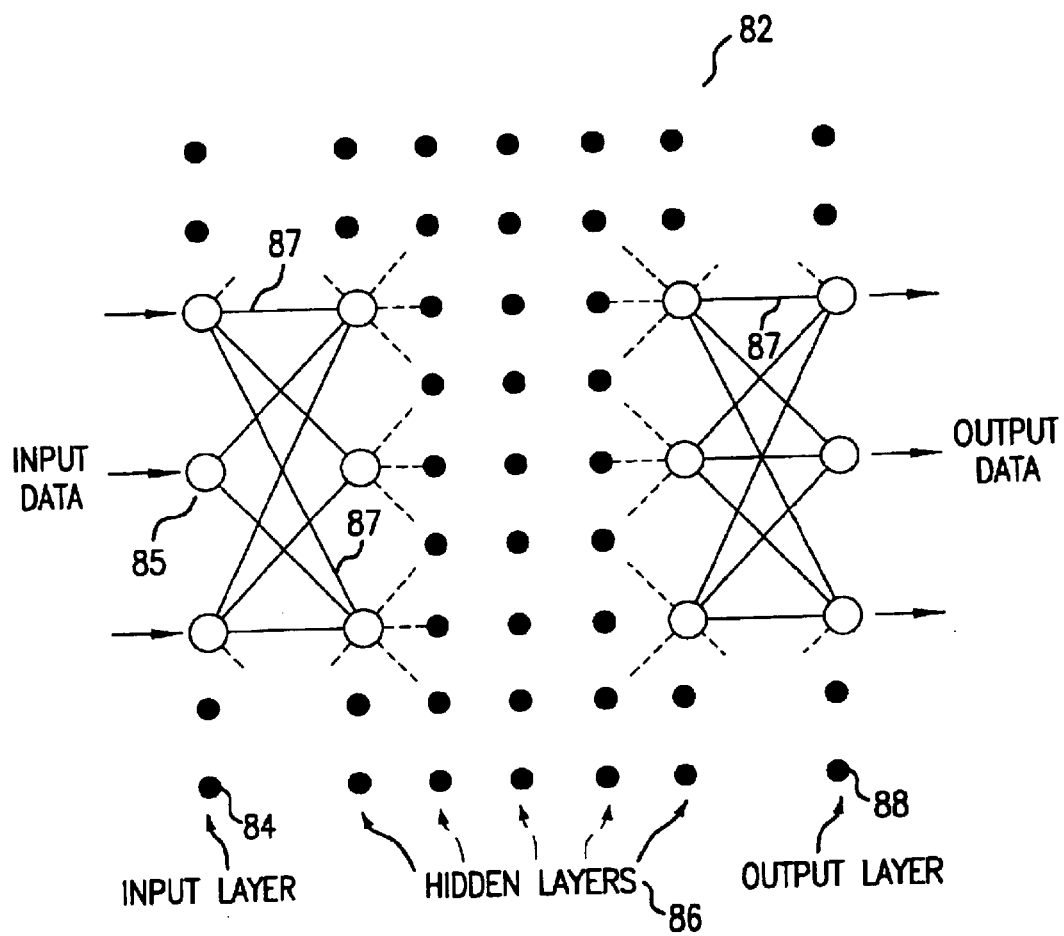
FIG. 8 is a diagram of the basic structure of an artificial neural network having a layered structure.

Artificial neural networks loosely model the functioning of a biological neural network, such as the human brain. Accordingly, neural networks are typically implemented as computer simulations of a system of interconnected neurons. In particular, neural networks are hierarchical collections of interconnected processing elements configured, for example, as shown in FIG. 8. Specifically, FIG. 8 is a schematic diagram of a standard neural network 82 having an input layer 84 of processing elements, a hidden layer 86 of processing elements, and an output layer 88 of processing elements. The example shown in FIG. 8 is merely an illustrative embodiment of a neural network 82 that can be used in accordance with the present invention. Other embodiments of a neural network 82 can also be used, as discussed next.

Turning next to the structure of a neural network 82, each of its processing elements receives multiple input signals, or data values, that are processed to compute a single output. The output value is calculated using a mathematical equation, known in the art as an activation function or a transfer function that specifies the relationship between input data values. As known in the art, the activation function may include a threshold, or a bias element. As shown in FIG. 8, the outputs of elements at lower network levels are provided as inputs to elements at higher levels. The highest level element, or elements, produces a final system output, or outputs.

In the context of the present invention, the neural network 82 is a computer simulation that is used to produce a recommendation of the desired ventilator setting of the ventilator controls 30 of the ventilator 20 which will adequately, and preferably optimally, support the physiological ventilation support needs of the patient, based upon at least a portion of the available ventilation setting parameters 42 and at least a portion of the ventilation data output signal 75 (i.e., at least a portion of the derived ventilation data 72).

The neural network 82 of the present invention may be constructed by specifying the number, arrangement, and connection of the processing elements which make up the network 82. A simple embodiment of a neural network 82 consists of a fully connected network of processing elements. The processing elements of the neural network 82 are grouped into layers: an input layer 84 where at least a portion of selected ventilation data 72, output signals 51, and the selected ventilator setting parameter signals 42 are introduced; a hidden layer 86 of processing elements; and an output layer 88 where the resulting determined level setting(s) for the control(s) 30 is produced. The number of connections, and consequently the number of connection weights, is fixed by the number of elements in each layer.

In a preferred embodiment of the present invention, the data types provided at the input layer may remain constant. In addition, the same mathematical equation, or transfer function, is normally used by the elements at the middle and output layers. The number of elements in each layer is generally dependent on the particular application. As known in the art, the number of elements in each layer in turn determines the number of weights and the total storage needed to construct and apply the neural network 82. Clearly, more complex neural networks 82 generally require more configuration information and therefore more storage.

In addition to the structure illustrated in FIG. 6A, the present invention contemplates other types of neural network configurations for the neural network module such as the example shown in FIG. 6B, which is described in more detail below. All that is required by the present invention is that a neural network 82 be able to be trained and retrained, if necessary, for use to determine the desired level settings of the controls 30 of the ventilator 20. It is also preferred that the neural network 82 adapt (i.e., learn) while in operation to refine the neural network's 82 determination of the appropriate level settings for the controls 30 of the ventilator 20.

Referring back to FIGS. 6A and 8, the operation of a specific embodiment of a feedforward neural network 82 is described in more detail. It should be noted that the following description is only illustrative of the way in which a neural network 82 used in the present invention can function. Specifically, in operation, at least a portion of selected ventilation data 72 from the ventilation data output signal 75 and the selected ventilator setting parameter signals 42 (i.e., collectively the input data) is provided to the input layer 84 of processing elements, referred to hereafter as inputs. The hidden layer elements are connected by links 87 to the inputs, each link 87 having an associated connection weight. The output values of the input processing elements propagate along these links 87 to the hidden layer 86 elements.

Each element in the hidden layer 86 multiplies the input value along the link 87 by the associated weight and sums these products over all of its links 87. The sum for an individual hidden layer element is then modified according to the activation function of the element to produce the output value for that element. In accordance with the different embodiments of the present invention the processing of the hidden layer elements can occur serially or in parallel.

If only one hidden layer 86 is present, the last step in the operation of the neural network is to compute the output(s), or the determined level setting(s) of the control(s) 30 of the ventilator by the output layer element(s). To this end, the output values from each of the hidden layer processing elements are propagated along their links 87 to the output layer element. Here, they are multiplied by the associated weight for the link 87 and the products are summed over all links 87. The computed sum for an individual output element is finally modified by the transfer function equation of the output processing element. The result is the final output or outputs which, in accordance with a preferred embodiment of the present invention, is the desired level setting or settings of the ventilator setting controls 30.

In the example of the intelligence subsystem 80 shown in FIG. 6B, the intelligence subsystem 80 is a hybrid intelligence subsystem that contains both rule-based modules 90 as well as neural networks 82. In this alternative embodiment of the intelligence subsystem 90, the determination of the desired level settings of the controls 30 of the ventilator 20 are broken down into a number of tasks that follow classical clinical paradigms. Each task may be accomplished using a rule-based system 90 or a neural network 82. In the preferred configuration, the determination of desired level settings of the ventilator setting controls 30 are performed by one of a series of neural networks 82.

The purpose of the ventilation status module 92 is to make an initial assessment of the adequacy of the ventilation support being provided to the patient P based on the level settings of the ventilator setting controls 30 (as inputted to the intelligence subsystem by the ventilator setting parameter signals 42) and the ventilation data output signal. The final determination of the desired level settings of the ventilator setting controls 30 is accomplished by one of a series of available neural networks 82 in the ventilator control setting predictor module 94. The purpose of the rule-based front end 96 is to determine, based on inputs from the ventilation status module 92, data entered by the operator, and the ventilator setting parameter signal 42, which of the available neural networks 82 will determine the desired level settings of the ventilator setting controls 30. The rule-based front end 96 will also determine which inputs are extracted from the ventilation data output signal 75 and presented to the selected neural network 82. Inputs to the ventilator control setting predictor module 94 include ventilator data 72 from the ventilation data output signal 75, user input, and input from the ventilator setting parameter signals 42. The purpose of the rule-based back end module 98 is to organize information from previous modules, neural networks 82, user input, and ventilation data 72 in the ventilation data output signal and to format the information for display on the visual display 62 as well as for storage to an external storage 64 such as a disk file.

As with most empirical modeling technologies, neural network development requires a collection of data properly formatted for use. Specifically, as known in the art, input data and/or the outputs of intermediate network processing layers may have to be normalized prior to use. It is known to convert the data to be introduced into the neural network 82 into a numerical expression, to transform each of the numerical expressions into a number in a predetermined range, for example by numbers between 0 and 1. Thus, the intelligent subsystem of the present invention preferably has means for: i) selecting at least a portion of the ventilation data 72 from the ventilation data output signal 75 and at least a portion of the ventilator setting parameter signals 42, ii) converting the selected portion of the ventilation data 72 and the selected portion of the ventilator setting parameter signals 42 into numerical expressions, and iii) transforming the numerical expressions into a number in a predetermined range.

In one conventional approach which can also be used in the present invention, the neural network 82 of the present invention may include a preprocessor 83. The preprocessor 83 extracts the correct data from the processing subsystem memory 48 and normalizes each variable to ensure that each input to the neural network 82 has a value in a predetermined numerical range. Once the data has been extracted and normalized, the neural network 82 is invoked. Data normalization and other formatting procedures used in accordance with the present invention are known to those skilled in the art and will not be discussed in any further detail.

In accordance with a preferred embodiment of the present invention the neural network 82 is trained by being provided with the ventilator control setting assessment made by a physician and with input data, such as ventilation data 72, the ventilation control setting parameter signals 42, and the output signals 51 that were available to the physician. In the sequel, the assessment along with the corresponding input measurement and input data is referred to as a data record. All available data records, possibly taken for a number of different patients, comprise a data set. In accordance with the present invention, a data set corresponding is stored in memory and is made available for use by the processing subsystem 40 for training and diagnostic determinations.

A typical training mechanism used in a preferred embodiment of the present invention is briefly described next. Generally, the specifics of the training process are largely irrelevant for the operation of the ventilation monitor system. In fact, all that is required is that the neural network 82 be able to be trained and retrained, if necessary, such that it can be used to determine acceptably accurate determinations of desired level settings of the controls 30 of the ventilator 20. Neural networks 82 are normally trained ahead of time using data extracted from patients 12 by other means. Using what it has learned from the training data, the neural network 82 may apply it to other/new patients P.

As known in the art, a myriad of techniques has been proposed in the past for training feedforward neural networks. Most currently used techniques are variations of the well-known error back-propagation method. The specifics of the method need not be considered in detail here. For further reference and more detail the reader is directed to the excellent discussion provided by Rumelhardt et al. in "Parallel Distributed Processing: Explorations in the Microstructure of Cognition," vols. 1 and 2, Cambridge: MIT Press (1986), and "Explorations in Parallel Distributed Processing, A Handbook of Models, Programs, and Exercises," which are incorporated herein in their entirety by reference.

Briefly, in its most common form back-propagation learning is performed in three steps:

1. Forward pass;
2. Error back-propagation; and
3. Weight adjustment.

As to the forward pass step, in accordance with the present invention a single data record, which may be extracted from the ventilation data output signal 75 and the ventilator setting parameter signal(s) 42, is provided to the input layer 84 of the network 82. This input data propagates forward along the links 87 to the hidden layer elements which compute the weighted sums and transfer functions, as described above. Likewise, the outputs from the hidden layer elements are propagated along the links to the output layer elements. The output layer elements computes the weighted sums and transfer function equations to produce the desired ventilator control settings 30.

In the following step of the training process, the physician assessment associated with the data record is made available. At that step, the determination of the desired level settings of the ventilator controls 30 produced by the neural network 82 is compared with the physician's assessment. Next, an error signal is computed as the difference between the physician's assesment and the neural network's 82 determination. This error is propagated from the output element back to the processing elements at the hidden layer 86 through a series of mathematical equations, as known in the art. Thus, any error in the neural network output is partially assigned to the processing elements that combined to produce it.

As described earlier, the outputs produced by the processing elements at the hidden layer 86 and the output layer 88 are mathematical functions of their connection weights. Errors in the outputs of these processing elements are attributable to errors in the current values of the connection weights. Using the errors assigned at the previous step, weight adjustments are made in the last step of the back-propagation learning method according to mathematical equations to reduce or eliminate the error in the neural network determination of the desired level setting of the ventilator setting controls 30.

The steps of the forward pass, error back-propagation, and weight adjustment are performed repeatedly over the records in the data set. Through such repetition, the training of the neural network 82 is completed when the connection weights stabilize to certain values that minimize, at least locally, the determination errors over the entire data set. As one skilled in the art will appreciate however, the neural network 82 may, and preferably will, continue to train itself (i.e., adapt itself) when placed into operational use by using the data sets received and stored in the memory of the processing subsystem 40 during operational use. This allows for a continual refinement of the monitor 10 as it is continually learning, i.e., training, while in operational use. Further, it allows for the continual refinement of the determination of the appropriate ventilator level settings in regard to the particular patient P to which the ventilator 20 is operatively attached.

In addition to back-propagation training, weight adjustments can be made in alternate embodiments of the present invention using different training mechanisms. For example, as known in the art, the weight adjustments may be accumulated and applied after all training records have been presented to the neural network 82. It should be emphasized, however, that the present invention does not rely on a particular training mechanism. Rather, the preferred requirement is that the resulting neural network 82 produce acceptable error rates in its determination of the desired level settings of the ventilator setting controls 30.

Upon completion of the determination of the desired level settings of the ventilator setting controls 30 by the intelligent subsystem 80 of the processing system 40, the desired level settings of the ventilator setting controls 30 may be displayed on the visual display 62 for use by the physician. The stored ventilation data output signal 75, and particularly the subset of the ventilation data output signal 75 containing the ventilation data 72 that was used by the intelligent subsystem 80 in the determination of the desired level setting of the controls 30, may be provided to the visual display 62. Also, the stored ventilator setting parameter signals 42 and the stored output signals 51 may be displayed on the visual display 62 in an appropriate format. At this point, the physician can review the results to aid in her or his assessment of the desireablity of the recommended desired level settings of the ventilator setting controls 30. The displayed results can be printed on printer [not shown] to create a record of the patient's condition. In addition, with a specific preferred embodiment of the present invention, the results can be communicated to other physicians or system users of computers connected to the ventilator monitor system 10 via an interface (not shown), such as for example a modem or other method of electronic communication.

Additionally, a preferred embodiment the present invention provides a real-time ventilator monitor system 10 and method. Real-time operation demands, in general, that input data be entered, processed, and displayed fast enough to provide immediate feedback to the physician in the clinical setting. In alternate embodiments, off-line data processing methods can be used as well. In a typical off-line operation, no attempt is made to respond immediately to the physician. The measurement and interview data in such case is generated some time in the past and stored for retrieval and processing by the physician at an appropriate time. It should be understood that while the preferred embodiment of the present invention uses a real-time approach, alternative embodiments can substitute off-line approaches in various steps.

The preferred method of operation of the present invention comprises the steps of receiving at least one ventilator setting parameter signal 42 indicative of the current level settings of the controls 30 of the ventilator 20, monitoring a plurality of output signals 51 to determine the sufficiency of ventilation support supplied to the patient P, determining the desired level settings of the ventilator setting controls 30, and displaying the desired level settings of the controls 30 to the operating clinician.

The output signals 51 received may comprise a plurality of signals selected from a group of: an exhaled carbon dioxide signal indicative of the exhaled carbon dioxide ($ExCO_2$) level of the exhaled gas expired by the patient P within the breathing circuit 22; a flow rate signal indicative of the flow rate (V) of the inhaled/exhaled gas expired by patient P within the breathing circuit 22; a pulse oximeter hemoglobin oxygen saturation ($SpO_2$) signal indicative of the oxygen saturation level of the patient P; a pressure (P) signal indicative of the pressure of the breathing gas within the breathing circuit 22; a blood pressure (BP) signal indicative of the blood pressure of the patient12. The output signals 51 may also comprise a temperature (T) signal indicative of the core body temperature of the patient P, an arterial blood gas $PaO_2$ signal, an arterial blood gas $PaCO_2$ signal, and/or an arterial blood gas pH signal.

The ventilator setting parameter signal 42 may comprise at least one of: a minute ventilation ($V_E$) signal indicative of the $V_E$ level set on the ventilator 20; a ventilator breathing frequency (f) signal indicative of the f level set on the ventilator 20; a tidal volume ($V_T$) signal indicative of the $V_T$ level set on the ventilator 20; a breathing gas flow rate (V) signal indicative of the V level set on the ventilator 20; a pressure limit signal indicative of the pressure limit set on the ventilator 20; a work of breathing (WOB) signal indicative of the WOB level set on the ventilator 20; a pressure support ventilation (PSV) signal indicative of the PSV level set on the ventilator 20; a positive end expiratory pressure (PEEP) signal indicative of the PEEP level set on the ventilator 20; a continuous positive airway pressure (CPAP) signal indicative of the CPAP level set on the ventilator 20; and a fractional inhaled oxygen concentration (FIO2) signal indicative of the FIO2 level set on the ventilator 20.

For example, the step of determining the desired level settings of the ventilator setting controls 30 of the ventilator 20 may comprise the steps of generating ventilation data 72 from the received output signals 51 in the processing subsystem 40 and applying at least a portion of the generated ventilation data 72 and the ventilator setting parameter signal 42 to the neural network 82 of the processing subsystem 40. If desired, at least a portion of the output signals 51 may also be applied to the neural network 82 as ventilation data 72.

In an alternative example, the step of determining the desired level settings of the controls 30 of the ventilator 20 may comprise the steps of generating ventilation data 72 from the received output signals 51 in the processing subsystem 40, applying a set of decision rules in the rule based front-end 96 to at least a portion of the ventilation data 72 and the ventilator setting parameter signal 42 to classify the applied portions of the ventilation data 72 and the ventilator setting parameter signal 42, selecting an appropriate neural network 82 to use, and applying a portion of the ventilation data 72 and the ventilator setting parameter signal 42 to the selected neural network 82 which will be used to determine the desired level settings of the ventilator setting controls 30.

The ventilator monitor system 10 of the present invention may be implemented in one of many different configurations. For example, the ventilator monitor system 10 may be incorporated within a ventilator 20. In an alternative example, the ventilator monitor system 10 may be a stand alone monitor that is operatively connected to the ventilator 20.

Figure 7:
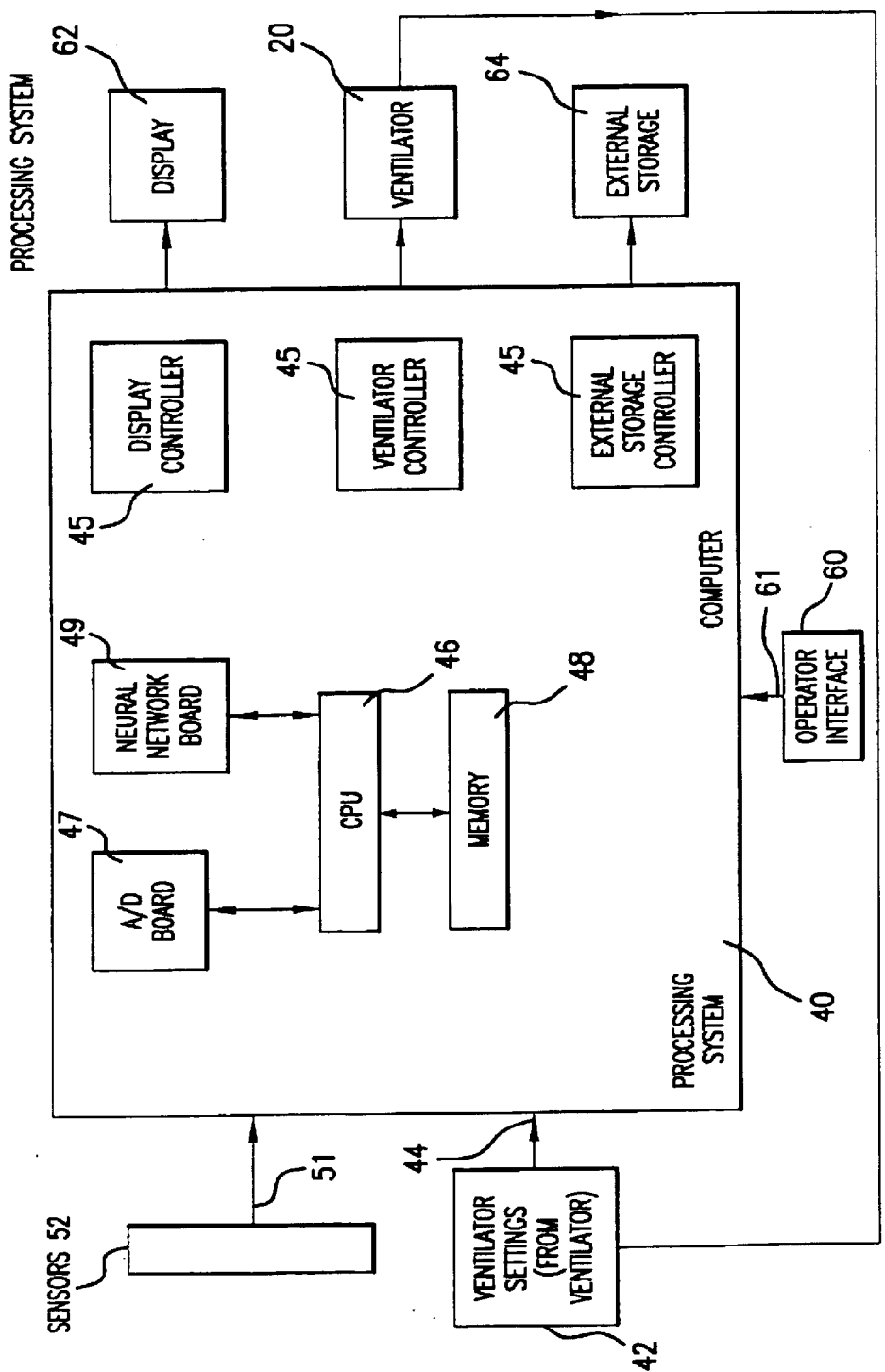
FIG. 7 is a schematic block diagram of one realization of the system of the invention.

A realization of an embodiment of the processing subsystem 40 of the present invention is illustrated in FIG. 7. Here, the processing subsystem 40 includes the processor 46, which is preferably a microprocessor, memory 48, storage devices 64, controllers 45 to drive the display 62, storage 64, and ventilator 20, and an analog-to-digital converter (ADC) 47 if required. The processing subsystem 40 also includes a neural network 82, which may, for example, be embodied in a neural network board 49. The ADC and neural network boards 47, 49 are commercially available products. There is also an optional output board (not shown) for connection to a computer network and/or central monitoring station.

The ADC board 47 converts the analog signal received from the output of any of the sensors 52 of the measuring means to a digital output that can be manipulated by the processor 46. In an alternative implementation, the output of any of the sensors 52 could be connected to the processor 46 via digital outputs, e.g., a serial RS232 port. The particular implementation is determined by the output features of the particular sensor 52. The processor 46 should contain circuits to be programmed for performing mathematical functions, such as, for example, waveform averaging, amplification, linearization, signal rejection, differentiation, integration, addition, subtraction, division and multiplication, where desired. The processor 46 may also contain circuits to be programmed for performing neural/intelligent control software, neural network learning software, and ventilator control software, as required. Circuits or programs performing these functions are well known to one skilled in the art, and they form no part of the present invention. The processor 46 executes the software which makes the computations, controls the ADC and neural network boards 47, 49, and controls output to the display and storage devices 62, 64, network communication, and the ventilator apparatus 20.

The purpose of the neural network board 49 is to implement the neural/intelligent control software. As one skilled in the art will appreciate, the need for a separate neural network board 49 is determined by the computational power of the main processor 46. With recent increases in microprocessor speeds, it may not be necessary to have a separate board 49, since some or all of these functions could be handled by the processor 46. The need for the separate board 49 is also determined by the precise platform on which the invention is implemented.

In addition, while the processor 46 of the processing subsystem 40 has been described as a single microprocessor, it should be understood that two or more microprocessors could be used dedicated to the individual functions. For example, the ventilator 20 may have a microprocessor that is operatively coupled to the processing subsystem 40 of the monitor system 10. In this manner the monitor system 20 could be incorporated into a modular system 10 that may be coupled to any conventional microprocessor-controlled ventilator 20 for monitoring of the ventilation support provided by the ventilator 20. Alternatively, as one skilled in the art will appreciate, and as shown in FIG. 2B, the monitor system 10 of the present invention may be incorporated into the design of a microprocessor-controlled ventilator 10 with the processing subsystem 40 of the ventilator monitor system using the microprocessor of the ventilator 20. In addition, the functions of the processor 46 could be achieved by other circuits, such as application specific integrated circuits (ASIC), digital logic circuits, a microcontroller, or a digital signal processor.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modification, both as to equipment details and operating procedures can be effected without departing from the scope of the invention itself. Further, it should be understood that, although the present invention has been described with reference to specific details of certain embodiments thereof, it is not intented that such details should be regarded as limitations upon the scope of the invention except as and to the extent that they are included in the accompanying claims.

What is claimed is:

1. A method for monitoring ventilation support for a patient having an airway, where said method comprises:

(1) utilizing a monitoring system comprising:

(a) a plurality of measuring sensors that monitor the patient, or that monitor a breathing circuit coupled to the airway of the patient, each measuring sensor generating an output signal, and (b) an intelligence system that receives at least one of the output signals, wherein the intelligence system evaluates at least one output signal to determine the appropriateness of ventilation for the patient;

(2) receiving into the intelligence system at least one of the signals;

(3) implementing the intelligence system, without clinician input, to evaluate the at least one output signal to determine the appropriateness of ventilation for the patient; and (4) recommending, without clinician input, a setting for at least one of the plurality of ventilator setting controls based on the evaluation of the at least one output signal by the intelligence system, wherein said setting is appropriate for the patient at that particular time.

2. The method of claim 1, further comprising providing a ventilator adapted to supply a gas to a patient via a breathing circuit in fluid communication with at least one lung of the patient, wherein the ventilator is operatively connected to the intelligence system, and wherein the ventilator includes a plurality of ventilator sorting controls, wherein each ventilator setting control controls a parameter relating to the supply of gas from the ventilator to the patient.

3. The method claim 2, further comprising:

causing the ventilator to generate a ventilator parameter signal indicative of a parameter related to the supply of gas from the ventilator to the patient; and providing the ventilator parameter signal to the intelligence system, wherein the intelligence system evaluates the at least one output signal and the ventilator parameter signal to determine the appropriateness of ventilation.

4. The method of claim 2, further comprising adjusting at least one of the plurality of ventilator setting controls based on the setting determined in the recommending step.

5. The method of claim 1, wherein said output signals are selected from the group consisting of: an exhaled carbon dioxide signal indicative of the exhaled carbon dioxide (ExCO2) level of the exhaled gas expired by the patient within the breathing circuit; a flow rate signal indicative of the flow rate (V) of the inhaled/exhaled gas expired by the patient within the breathing circuit; a pulse oximeter hemoglobin oxygen saturation (SpO2) signal indicative of the oxygen saturation level of the patient; a pressure (P) signal indicative of the pressure of the breathing gas within the breathing circuit; a blood pressure (BP) signal indicative of the blood pressure of the patient; and a temperature (T) signal indicative of the core body temperature of the patient.

6. The method of claim 5, wherein the output signals also include at least one of the group consisting of: an arterial blood gas PaO2 signal; an arterial blood gas PaCO2signal; and an arterial blood gas pH signal.

7. The method of claim 1, wherein the ventilator parameter signals include at least one of the group consisting of: a minute ventilation ($V_E$) signal; a ventilator breathing frequency of (f) signal; a tidal volume ($V_T$) signal; a breathing gas flow rate (V) signal; a pressure limit signal; a work of breathing (WOB) signal; a pressure support ventilation (PSV) signal; a positive end expiratory pressure (PEEP) signal; a continuous positive airway pressure (CPAP) signal; and a fractional inhaled oxygen concentration (FIO2) signal.

8. The method of claim 1, further comprising displaying the recommended settings of the ventilator setting controls.

9. The method of claim 1, wherein the intelligence system comprises a neural network, and wherein recommending the settings of the ventilator setting controls of the ventilator comprises applying at least a portion of the output signals and the ventilator parameter signals to the neural network of the intelligence system to determine the recommended settings of the ventilator setting controls.

10. The method of claim 1, wherein comprising:

selecting output signals for display; and displaying the selected output signals in real time.

11. The method of claim 1, further comprising displaying at least one of the recommended ventilator setting control settings.

12. The method of claim 1, wherein the intelligence system is programmed with a set of decision rules.

* * * * *

UNITED STATES PATENT AND TRADEMARK OFFICE
CERTIFICATE OF CORRECTION

PATENT NO.    : 6,796,305 B1
DATED         : September 28, 2004
INVENTOR(S)   : Banner et al.

It is certified that error appears in the above-identified patent and that said Letters Patent is hereby corrected as shown below:

Column 3,
Line 62, "modem" should read -- modern --.

Column 4,
Line 8, "modem" should read -- modern --.

Column 6,
Line 3, "(SIMY);" should read -- (SIMV); --.
Line 60, "least. one" should read -- least one --.

Column 7,
Line 40, "a-plurality" should read -- a plurality --.

Column 8,
Line 18, "attache dot" should read -- attached to --.
Line 21, "to, the arm" should read -- to the arm --.
Line 25, "data maybe" should read -- data may be --.
Line 25, "derived form" should read -- derived from --.

Column 10,
Line 30, "sun of" should read -- sum of --.

UNITED STATES PATENT AND TRADEMARK OFFICE
CERTIFICATE OF CORRECTION

PATENT NO. : 6,796,305 B1
DATED : September 28, 2004
INVENTOR(S) : Banner et al.

It is certified that error appears in the above-identified patent and that said Letters Patent is hereby corrected as shown below:

Column 19,
Line 2, "the signals;" should read -- the output signals; --.
Line 17, "sorting controls," should read -- setting controls, --.

Column 20,
Line 30, "wherein comprising:" should read -- further comprising: --.

Signed and Sealed this

Fourth Day of October , 2005

JON W. DUDAS
*Director of the United States Patent and Trademark Office*